(12) United States Patent
Brown

(10) Patent No.: US 8,090,566 B2
(45) Date of Patent: Jan. 3, 2012

(54) BATTERY LONGEVITY MONITORING

(75) Inventor: Timothy R. Brown, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 724 days.

(21) Appl. No.: 12/061,807

(22) Filed: Apr. 3, 2008

(65) Prior Publication Data

US 2009/0254356 A1    Oct. 8, 2009

(51) Int. Cl.
*G06F 17/50* (2006.01)
*A61N 1/00* (2006.01)
*H02J 7/00* (2006.01)

(52) U.S. Cl. ............................... 703/13; 607/29; 320/134

(58) Field of Classification Search .................... 703/13; 607/29; 320/134, 136, 137, 157, 159
See application file for complete search history.

(56) References Cited

U.S. PATENT DOCUMENTS

| | | | |
|---|---|---|---|
| 4,556,061 A | 12/1985 | Barreras et al. | |
| 4,715,381 A | 12/1987 | Moberg | |
| 5,137,020 A | 8/1992 | Wayne et al. | |
| 5,391,193 A | 2/1995 | Thompson | |
| 5,402,070 A | 3/1995 | Shelton et al. | |
| 5,458,624 A | 10/1995 | Renirie et al. | |
| 5,579,033 A | 11/1996 | Rutledge et al. | |
| 5,620,474 A | 4/1997 | Koopman | |
| 5,741,307 A | 4/1998 | Kroll | |
| 5,800,472 A | 9/1998 | Mann | |
| 6,108,579 A * | 8/2000 | Snell et al. | 607/29 |
| 6,129,746 A | 10/2000 | Levine et al. | |
| 6,167,309 A | 12/2000 | Lyden | |
| 6,671,552 B2 | 12/2003 | Merritt et al. | |
| 6,901,293 B2 | 5/2005 | Rogers et al. | |
| 2003/0065366 A1 | 4/2003 | Merritt et al. | |
| 2004/0039424 A1* | 2/2004 | Merritt et al. | 607/29 |
| 2004/0064161 A1 | 4/2004 | Gunderson et al. | |
| 2004/0199146 A1 | 10/2004 | Rogers et al. | |
| 2005/0256548 A1 | 11/2005 | Rogers et al. | |
| 2006/0024706 A1 | 2/2006 | Ghosh et al. | |
| 2008/0177345 A1* | 7/2008 | Schmidt et al. | 607/29 |

* cited by examiner

*Primary Examiner* — Paul Rodriguez
*Assistant Examiner* — Andre Pierre Louis

(57) ABSTRACT

Systems and methods are provided that estimate when to replace a medical device that is implanted in a patient due to battery depletion. These systems and methods significantly reduce the need for service calls made to medical device manufacturers that relate to battery longevity. In some examples, these systems and methods estimate a battery end of life based, at least in part, on an actual battery voltage received on an actual transmission date and a model transmission date determined based on the actual battery voltage. The estimated battery end of life is further based on a comparison of the model transmission date with the actual transmission date.

20 Claims, 9 Drawing Sheets

US 8,090,566 B2

BATTERY LONGEVITY MONITORING

FIELD

Some embodiments disclosed herein relate generally to monitoring the longevity of medical device batteries.

BACKGROUND

Medical devices run on batteries that, like other batteries, have a finite life span. In many cases, battery powered devices that are implanted in a patient must be replaced when the battery is depleted to a predetermined level. Presently, the voltage in a battery is monitored in real time with what may be called a "gas-gauge" type monitor. If the battery voltage falls below a threshold value, an audible alarm sounds, providing a notification to schedule a replacement procedure. Though the threshold value is chosen such that there is sufficient time to schedule the replacement procedure after the alarm sounds, the audible alarm often causes patient anxiety. Additionally, the audible alarm can cause inconvenience, or even embarrassment, if it is sounded in certain situations (e.g., in a movie theater, etc.).

Anticipating that anxiety, customers (e.g., physicians, nurses, technicians, physician's assistants, etc.) often make service calls to medical device manufacturers, asking for an estimate on battery life. A medical device manufacturer's technical support staff then often asks the customer for certain parameters concerning the medical device and/or the patient, applies a battery longevity model to those parameters, and provides an estimated replacement date to the customer. The volume of service calls that relate to battery longevity consumes a large amount of technical support resources.

SUMMARY

Embodiments described herein help estimate when to replace a device due to battery. Embodiments may include a computer-implemented method, a system, or a computer-readable medium programmed with instructions for causing a programmable processor to perform a method.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is illustrative in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1:
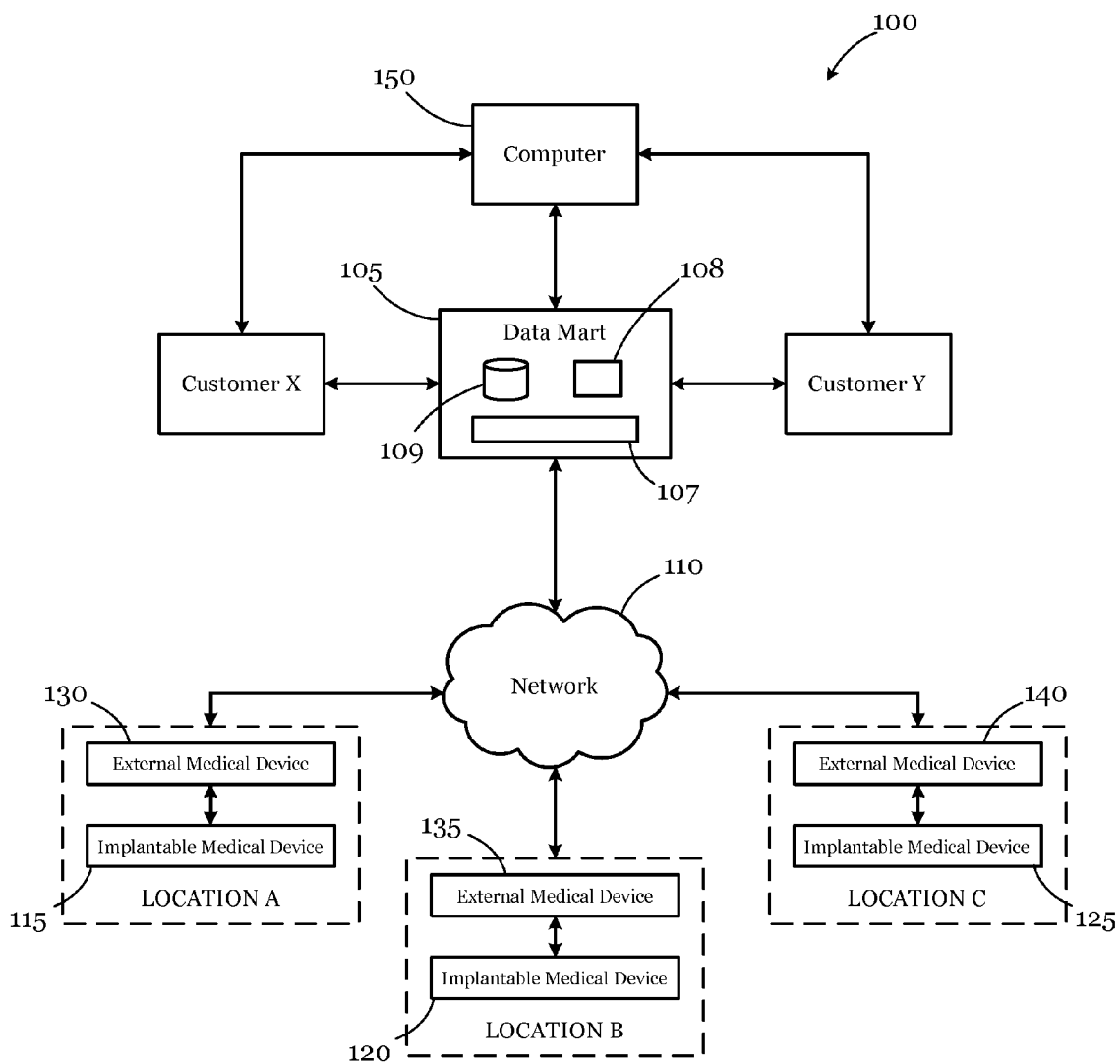
FIG. 1 is a schematic block diagram of an illustrative remote patient management system.

FIG. 1 shows an illustrative remote patient management system 100. The remote patient management system 100 forms part of a system used for remotely managing patients prescribed with medical monitoring or therapy delivery devices. The remote patient management system 100 allows customers to monitor multiple patients located at multiple locations. The illustrative remote patient management system 100 of FIG. 1 shows three locations—Location A, Location B, and Location C. Remote patient management systems are not, however, limited to three locations. Locations A, B, and C can represent, e.g., the residences of three patients. Some embodiments of the remote patient management system 100 allow customers to access data from patients' medical devices without those patients having to visit a clinical facility. The remote patient management system 200 saves valuable time—both for the participating customers and for the patients.

Many different kinds of customers interact with the illustrative remote patient management system 100. Such customers include physicians such as hematologists, interventional cardiologists, neurologists, endocrinologists, heart failure specialists, and others. FIG. 1 shows two illustrative customers—Customer X and Customer Y. Remote patient management systems are not, however, limited to two customers. Multiple customers can monitor and treat the same patient.

The illustrative remote patient management system 100 includes a data mart 105 located at a central location. The data mart 105 includes a central communication module 107, which allows the data mart 105 to communicate with other components. The central communication module 107 enables the data mart 105 to receive data transmissions from multiple remote medical devices for enabling remote patient management of a population of patients. The central communication module 107 enables the data mart 105 to provide information, such as instructions, to medical devices at multiple locations. The data mart 105 interacts with various types of equipment at each location through a network 110. The network 110 can be a local area network (LAN), a wide area network (WAN), or other suitable telecommunications network, including the Internet. The data mart 105 includes a processor 108 that operates with an associated central database 109. The central database 109 may store patient data and/or programs and algorithms used by the processor in performing patient management operations (e.g., programming and/or interrogating IMDs). The central database 109 can include electronic medical records in a relational database and can include data files and code used for controlling communication with external components.

An implantable medical device ("IMD") 115, 120, 125 (implanted inside of a patient) and an external medical device ("EMD") 130, 135, 140 are located remotely at each of Locations A, B, and C of the illustrative remote patient management system 100. The IMD 115, 120, 125 can be a cardiac stimulation device (e.g., a pacemaker), cardioverter/defibrillator (ICD), a cardiac monitor, a hemodynamic monitor, a neuromuscular stimulator, a drug delivery device, or other IMD. The IMD 115, 120, 125 at one location can be the same as or different than the IMD 115, 120, 125 at the other locations. The EMD 130, 135, 140 can be a remote home monitor, programmer, or other EMD. The EMD 130, 135, 140 collects various physiological indicators from IMD patients, such as weight, systemic blood pressure, symptoms, and others. The EMD 130, 135, 140 at one location can be the same or different than the EMD 130, 135, 140 at the other locations.

The data mart 105, the network 110, the IMD 115, 120, 125, and the EMD 130, 135, 140 can be configured to communicate in a variety of ways. In one example, the IMD 115, 120, 125 is configured to communicate with the EMD 130, 135, 140, which is configured to communicate with the data mart 105 via the network 110. In some embodiments, the IMD 115, 120, 125 is configured to communicate with the data mart 105 directly through the network 110. In some embodiments, the data mart 105 communicates directly with either the IMD 115, 120, 125 or the EMD 130, 135, 140 without use of the network 110. Communication between the data mart 105, the network 110, the IMD 115, 120, 125, and/or the EMD 130, 135, 140 can be, for example, bi-directional. The communication configuration can be the same or different with respect to Locations A, B, and C. In other words, in some embodiments, the data mart 105 is configured to communicate with Location B's IMD 120 through the network 110 while being configured to communicate with Location C's IMD 125 through the EMD 140 without the use of the network 110. Each communication among the data mart 105, the network 110, the IMD 115, 120, 125, and the EMD 130, 135, 140 can be initiated by the recipient of the communication ("pull") or by the transmitter ("push").

The content of the information being communicated between the data mart 105, the EMD 130, 135, 140, and the IMD 115, 120, 125 varies according to the particular application. In some applications, the IMD 115, 120, 125 provides data to the data mart 105. The IMD 115, 120, 125 can gather and/or store such data on a continuous or periodic basis. In some embodiments, the IMD 115, 120, 125 communicates some or all of that data to either the EMD 130, 135, 140 or the data mart 105. The EMD 130, 135, 140, for example, communicates some or all of the data received from the IMD 115, 120, 125 to the data mart 105. In some embodiments, the EMD 130, 135, 140 performs one or more processing operations on the data received from the IMD 115, 120, 125.

In many embodiments, the data mart 105 receives a large quantity of data from the IMD 115, 120, 125 and/or EMD 130, 135, 140. In some embodiments, the IMD 115, 120, 125 can gather and/or store information related to parameters such as device performance and various physiological indicators of a patient (e.g., heart rhythm, blood pressure, respiration, patient activity level, heart wall motion, blood chemistry, and the like). In some embodiments, approximately 4000 parameters are provided by the IMD 115, 120, 125 to the data mart 105. Examples of kinds of parameters include pacing parameters, therapy settings, diagnostic data, stored digitized episode data, counter data, and time stamps for various data information, and other relevant parameters. In many such embodiments, all of that data is provided to the data mart 105. Such a full transmission of data from the IMD 115, 120, 125 to the data mart 105 can occur on a periodic basis, according to a pre-selected schedule. For example, a full transmission can occur every 90 days. The data mart can index data received from the IMD 115, 120, 125 according to patient, transmission date, and/or any other factor that would aid in being able to access the data at a later date.

In some applications, the data mart 105 provides information to the IMD 115, 120, 125 and/or to the EMD 130, 135, 140. In one example, Customer X enters instructions related to, e.g., therapy, operating parameters, transfer code, or other instructions, into the data mart 105. The data mart 105 communicates those instructions to the IMD 115, 120, 125 and/or the EMD 130, 135, 140, either through the network 110 or directly.

The illustrative remote patient management system 100 includes a computer 150. In some embodiments, the computer 150 is located in the same location as the data mart 105. In some embodiments, the computer 150 is located remotely from data mart 105. The computer 150 can be a device, or multiple devices working together, that accepts information (in the form of digitalized data) and manipulates it for some result based on a program or sequence of instructions on how the data is to be processed. In some embodiments, the computer 150 may include storage for storing data for some necessary duration.

With the information corresponding to patients and their medical devices provided to the data mart 105, customers can access that information to remotely care for such patients. In many embodiments, when data is transmitted from a medical device to the data mart 105, all of that data is provided to the customer(s) caring for the corresponding patient without undergoing any processing. For example, if the patient at Location A transmits a full transmission from his/her IMD 115 to the data mart 105, that full transmission is often provided to Customer X and/or Customer Y. In some embodiments, the customer receives only a subset of the data provided to the data mart 105 in un-processed form. In some such embodiments, that subset of data can be selected according to a specific request by a customer. In some such embodiments, a program can determine the subset of data that is provided to a customer.

In many cases, the customer can access historical data in remotely caring for patients. For example, the patient at Location C can provide a full transmission related to IMD 125 to the data mart 105 on a transmission date, and the data mart can provide that information to Customer Y. If Customer Y then detected a potentially noteworthy, e.g., blood pressure level in the patient at Location C, Customer Y could retrieve information from the data mart 105 that had been transmitted by the patient at Location C to the data mart 105 at a previous date (e.g., 90 days earlier). Customer Y could then compare the patient's blood pressure on the transmission date with his/her blood pressure on the previous date before determining whether something should be done.

In certain embodiments, data in the data mart 105 can be processed before being provided to customers. In some embodiments, the data can be processed by the computer 150 and/or the processor 108 of the data mart 105. For example, rather than providing a full transmission of un-processed data to Customer X and having Customer X sort out the data to determine if the IMD's battery is depleting at a normal rate, the data can be processed by the processor 108 and/or the computer 150, and Customer X can be notified only if the data shows that the IMD's battery is depleting at an abnormal rate.

In some embodiments, un-processed data that is provided to the customer can be automatically processed, thereby giving customers access to processed data. For example, Customer Y's computer can receive a full transmission from the data mart 105 and can automatically assess battery longevity conditions. Customer Y can then be notified only if the data shows that the IMD's battery is depleting at an abnormal rate.

If the customer can access processed information related to battery longevity, he/she can often spend less time and energy monitoring for abnormal battery depletion. In this way, the customer is able to invest the extra resources he/she would have spent monitoring for abnormal IMD battery depletion in providing enhanced care for his/her patients.

Figure 2:
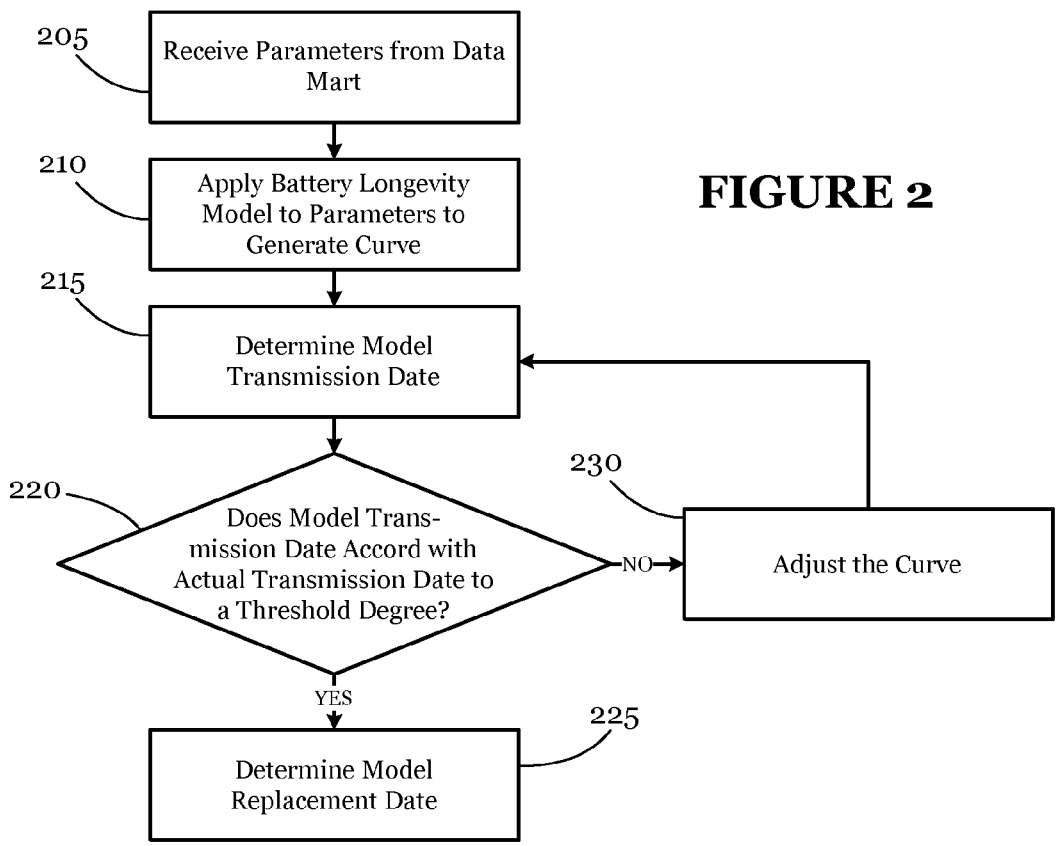
FIG. 2 is a flow chart of an illustrative method of estimating when to replace a battery of a medical device that is implanted in a patient.

In some embodiments, the computer 150, the processor 108 of the data mart 105, and/or a computer at one of the customer sites can have access to a computer-readable medium programmed with instructions for causing a programmable processor to perform one or more methods. FIG. 2 shows an illustrative method of estimating when to replace a battery of a medical device that is implanted in a patient. Using a method such as that of FIG. 2, a customer need not query for an estimate of when the battery might have to be replaced. Instead, in many cases, an estimated replacement date is determined, and the customer is notified only if that date is indicative of abnormal conditions. In such cases, customers can assume that the battery is depleting at a normal rate if they receive no information about battery longevity.

As shown, a plurality of parameters can be received from a data mart (205). A computer that is external to the data mart or a processor within the data mart can receive the parameters from the data mart. In many embodiments, at least some of the parameters received can have been provided by a medical device to the data mart on what may be called an actual transmission date (e.g., via a full transmission). The actual transmission date can correspond to how long the medical device had been implanted in the patient when the relevant parameters were provided to the data mart. The parameters can include an actual battery voltage value as of the actual transmission date. In some embodiments, the parameters can also include other information related to the medical device and/or to the patient (e.g., pacing mode; lower pace rate for A and V channels; sensing rate for A and V channels; A, RV, and LV pulse widths; amplitudes; resistance-percent paced; feature settings; EGM data; impedance measurements; auto capacitor reformation interval; months on setting; etc.). In some embodiments, roughly 22 parameters can be pulled from the data mart, though a greater or lesser number of parameters are possible.

Figure 3:
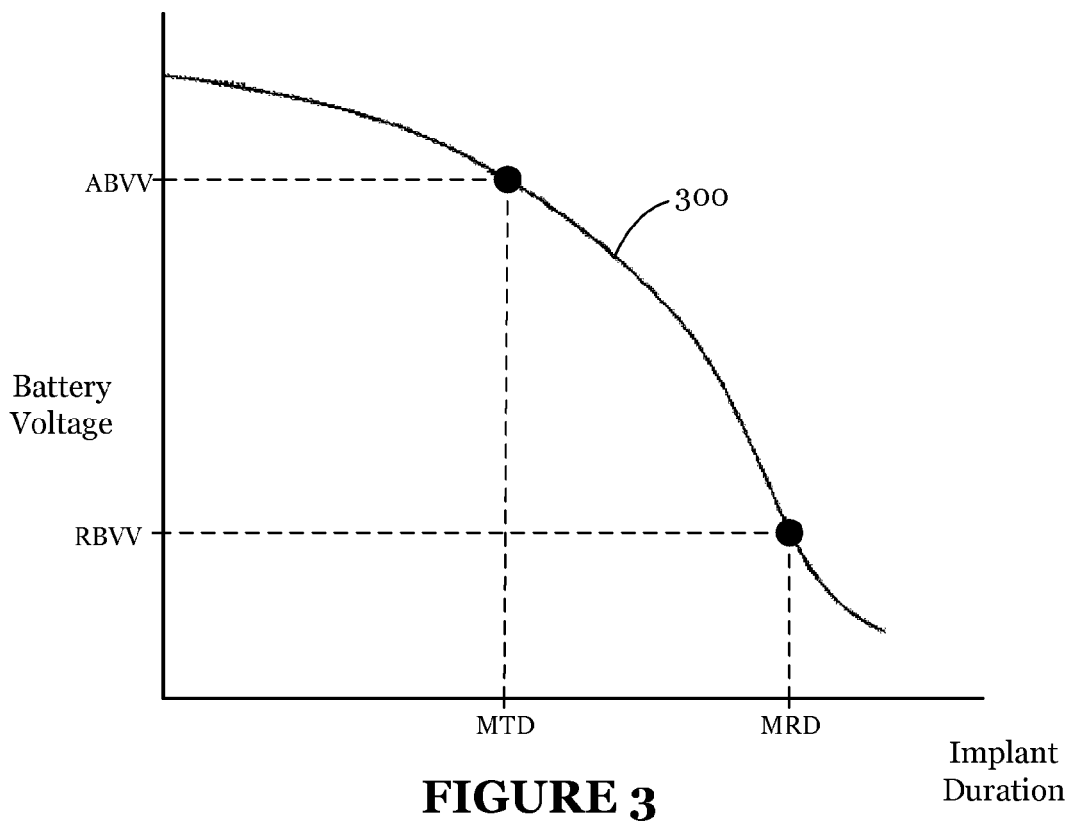
FIG. 3 is a graph showing an illustrative curve of a model battery voltage versus a model medical device implant duration.

After parameters are received from a data mart (205), a battery longevity model can be applied to at least some of the plurality of parameters to generate a curve (210). The curve can provide an estimate for how a medical device battery will deplete over its life. The battery longevity model that generates the curve can account for a variety of factors that impact how the battery will deplete. One such factor is current drain, or how hard the medical device is working. In most cases, the battery longevity model includes a model current drain input that corresponds to the degree of current drain commonly experienced by the particular medical device battery to which the battery longevity model pertains. FIG. 3 shows an illustrative curve 300 of a model battery voltage versus a model medical device implant duration.

Referring again to FIG. 2, a model transmission date can be determined (215). In most cases, the battery longevity model does not account for how long the medical device has actually been implanted. The model transmission date can correspond to how many days after implantation it would take for the battery voltage to deplete to the actual battery voltage value if the battery depleted according to the curve. As shown in FIG. 3, the model transmission date (MTD) can be determined by finding the actual battery voltage value (ABVV) on the curve 300. Referring again to FIG. 2, the model transmission date can be compared with the actual transmission date to determine whether the model transmission date accords with the actual transmission date to a threshold degree (220). In many embodiments, the threshold degree is based on the normal performance tolerance of the battery, meaning that the model transmission date accords with the actual transmission date when they are within a normal performance tolerance of each other. In this way, the actual transmission date can help verify the accuracy of the curve produced by the battery longevity model.

In many embodiments, when the model transmission date accords with the actual transmission date to a threshold degree, meaning that the curve is accurate at least to a satisfactory degree, a model replacement date can be determined (225). As shown in FIG. 3, the model replacement date (MRD) can be determined by finding a replacement battery voltage value (RBVV) on the curve 300. The replacement battery voltage value (RBVV) can be a known value indicating the level at which the medical device to which the battery longevity model pertains must be replaced to ensure optimum performance. For example, a high-rate battery for an implantable cardiac defibrillator can have a replacement battery voltage value of 2.625 volts, which can correspond to an end-of-life battery voltage of 2.550 volts. As is discussed in greater detail below, in some circumstances, the model replacement date (MRD) can be provided to a customer.

Figure 4:
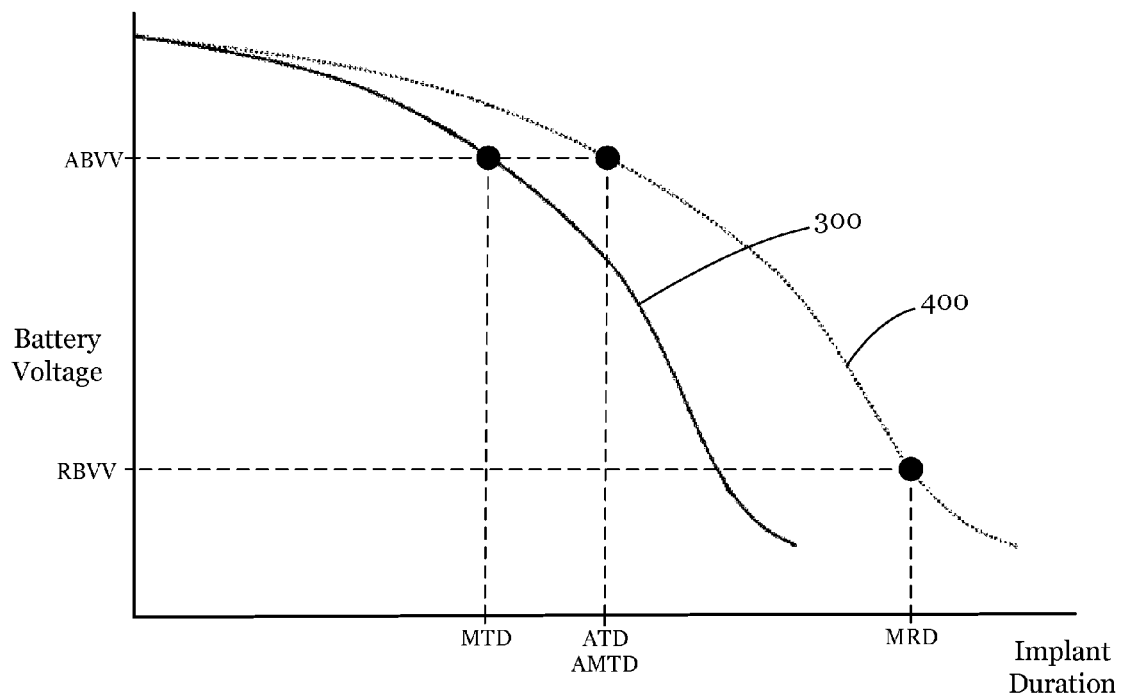
FIG. 4 is a graph showing an illustrative way to adjust a curve to determine a model replacement date.

Referring again to FIG. 2, if the model transmission date does not accord with the actual transmission date to a threshold degree, the curve can be adjusted (230) in one or more iterations until the model transmission date does accord with the actual transmission date to a threshold degree. In some embodiments, adjusting the curve can include modifying the model current drain input in the battery longevity model. FIG. 4 shows a situation in which the actual transmission date (ATD) is later than the model transmission date (MTD) that falls on curve 300. This often indicates that the pertinent medical device battery has experienced less current drain than the current drain input assumed by the battery longevity model. In such a situation, adjusting the curve can include decreasing the model current drain input to produce an adjusted curve reflecting a slower depletion rate. As shown in FIG. 2, a new model transmission date can be determined (215) and compared with the actual transmission date (220), as discussed above. FIG. 4 shows the final adjusted curve 400 with the adjusted model transmission date (AMTD) corresponding to the actual transmission date (ATD). As can be seen, the difference between the model replacement date (MRD) and the date on which the replacement battery voltage value (RBVV) intersects with curve 300 is significantly greater than the difference between the actual transmission date (ATD) and the model transmission date (MTD) of curve 300.

Figure 5:
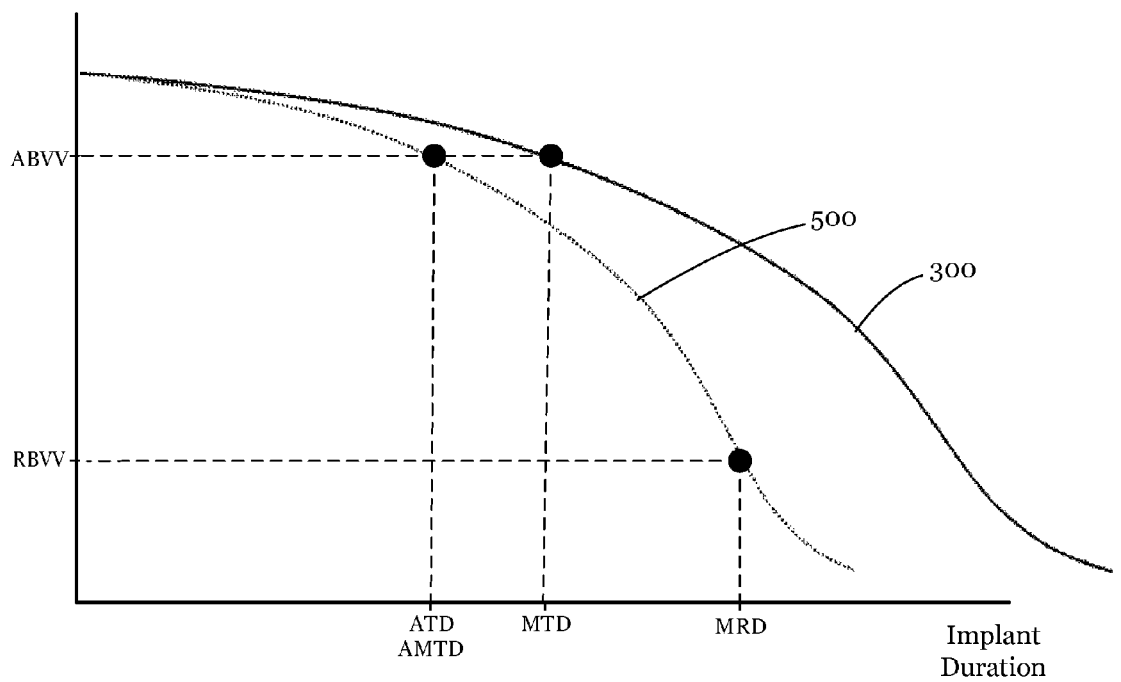
FIG. 5 is a graph showing an illustrative way to adjust a curve to determine a model replacement date.

In contrast to FIG. 4, FIG. 5 shows a situation in which the actual transmission date (ATD) is earlier than the model transmission date (MTD) that falls on curve 300. This often indicates that the pertinent medical device battery has experienced more current drain than the current drain input assumed by the battery longevity model. In such a situation, adjusting the curve can include increasing the model current drain input to produce an adjusted curve reflecting a faster depletion rate. If the model current drain input must be increased above a threshold level (e.g., to a current drain that is higher than could be expected in even an active medical device), a warning message can be communicated to one or more customers and/or to the patient. As shown in FIG. 2, a new model transmission date can be determined (215) and compared with the actual transmission date (220), as discussed above. FIG. 5 shows the final adjusted curve 500 with the adjusted model transmission date (AMTD) corresponding to the actual transmission date (ATD). Like FIG. 4, FIG. 5 shows that the difference between the model replacement date (MRD) and the date on which the replacement battery voltage value (RBVV) would intersect with curve 300 is significantly greater than the difference between the actual transmission date (ATD) and the model transmission date (MTD) of curve 300.

In some embodiments, the model replacement date that is determined by adjusting the curve may be less accurate if the actual transmission date is earlier than a threshold date (e.g., three months), meaning that the medical device has been implanted relatively recently. In many embodiments, the threshold date can correspond to recommended guidelines for follow-up/monitoring. Making changes to the curve to accommodate actual battery voltage values on the relatively flat part of the curve can cause disproportionate changes to the less flat parts of the curve. This can lead to inaccuracies in determining a model replacement date in some circumstances.

Figure 6:
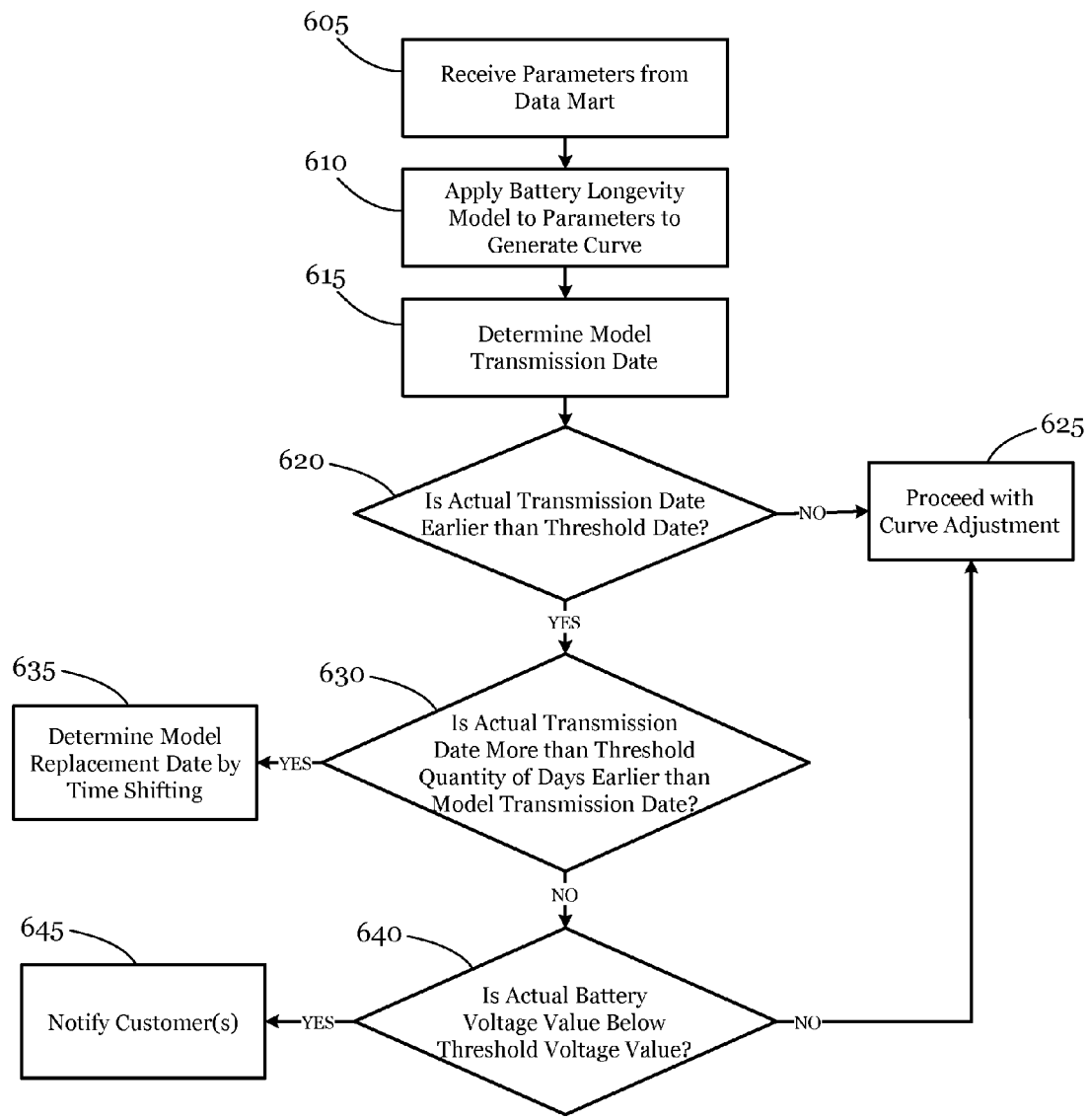
FIG. 6 is a flow chart of an illustrative method for enhancing the curve adjustment method of FIG. 2.

FIG. 6 shows an illustrative method for enhancing the curve adjustment method of FIG. 2. As with the method of FIG. 2, the method of FIG. 6 can be performed by a processor/computer according to instructions programmed in a computer-readable medium. The method of FIG. 6 includes receiving parameters from a data mart (605), applying a battery longevity model to at least some of the parameters to generate a curve (610), and determining a model transmission date (615). Such steps can have similar characteristics to corresponding steps in the method of FIG. 2.

Referring again to FIG. 6, the processor/computer performing the method can determine whether the actual transmission date is earlier than a threshold date (620). If the transmission date is not earlier than the threshold date, the processor/computer can proceed to the curve adjustment method of FIG. 2 (e.g., to step 220) (625). Referring again to FIG. 6, if the actual transmission date is earlier than the threshold date, it can be determined whether the actual transmission date is more than a threshold quantity of days earlier than the model transmission date (630). In many embodiments, the threshold date can correspond to recommended guidelines for follow-up/monitoring. For example, in some embodiments, the threshold quantity of days can be 15 days. In such embodiments, if the actual transmission date is more than 15 days earlier than the model transmission date for a recently implanted medical device, increasing the model current drain input can lead to a model replacement date that is premature, thereby increasing the number of false alarms about the medical device's performance.

Figure 7:
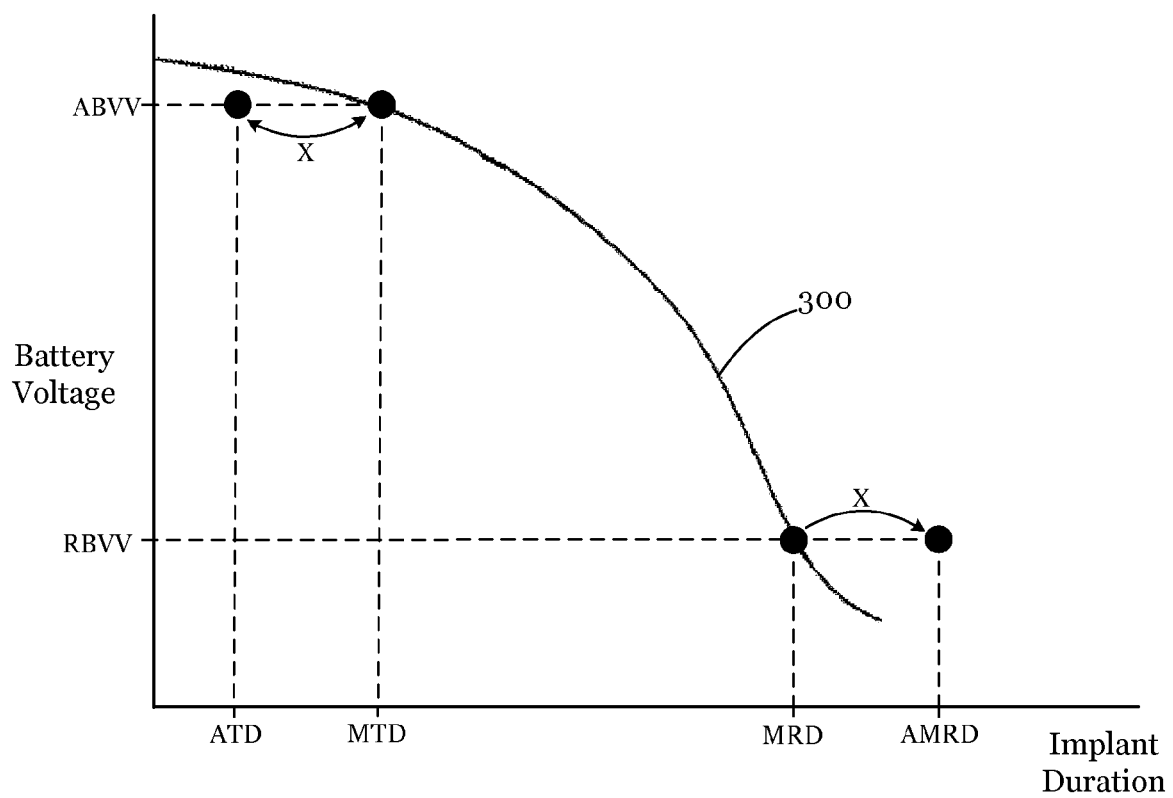
FIG. 7 is a graph showing an illustrative way to adjust a model replacement date by time shifting.

If it is determined that the actual transmission date is more than a threshold quantity of days earlier than the model transmission date, the model replacement date can be determined by time shifting (635). FIG. 7 provides an illustration of time shifting. As can be seen, the actual transmission date (ATD) is relatively early and also X days earlier than the model transmission date (MTD). For purposes of this illustration, assume that X days is more than the threshold quantity of days. Instead of adjusting the curve 300 so that the model transmission date (MTD) accords with the actual transmission date (ATD), the processor/computer can determine the model replacement date (MRD) without adjusting the curve 300. Then, the model replacement date (MRD) can be adjusted, e.g., by adding X days to the model replacement date (MRD), thereby producing an adjusted model replacement date (AMRD). In this way, the ratio of implant duration to estimated total service time increases only slightly, making the adjusted model replacement date (AMRD) more accurate and reducing the number of false alarms. In some embodiments, if the actual transmission date (ATD) is not more than a threshold quantity of days earlier than the model transmission date (MTD), the processor/computer can proceed to the curve adjustment method of FIG. 2 (e.g., to step 220).

Referring again to FIG. 6, in some embodiments, if actual transmission date is earlier than a threshold date, it can be determined whether the actual battery voltage value is below a threshold voltage value (640). In many embodiments, the threshold voltage value is based on a normal implant voltage value. For example, in some embodiments, the normal battery voltage value at implant is 3.25 volts. If the actual transmission date is less than, e.g., six months, the threshold voltage value for such a battery can be 2.999 volts. If it is determined that the actual battery voltage value is below the threshold voltage value for a recently implanted medical device, the appropriate customer(s) can be notified (645). If it is determined that the actual battery voltage value is not below the threshold voltage value for a recently implanted medical device, the processor/computer can proceed to the curve adjustment method of FIG. 2 (e.g., to step 220). In this way, batteries that were implanted with implant voltage values that were lower than normal can be identified, and appropriate actions can be taken.

Embodiments described herein can account for recently implanted medical devices in a variety of ways. Some can address situations in which the actual transmission date is more than a threshold quantity of days earlier than the model transmission date. Some can address situations in which the actual battery voltage is below a threshold voltage value. Some embodiments can address both of such kinds of situations.

In some embodiments, the model replacement date that is determined by adjusting the curve may be less accurate if the actual transmission date is more than a threshold quantity of days later than the model transmission date and the model current drain input is below a current drain threshold. In some embodiments, the threshold quantity of days can be based on a manufacturing "shelf period," which assumes that a medical device will be implanted within a certain period of time (e.g., five months) after manufacturing is complete. One example of a threshold quantity of days in some embodiments is 15 days. The current drain threshold can be based on the current drain experienced by the medical device in zero-workload conditions (e.g., 0% pacing in a pacemaker). One example of a current drain threshold in some embodiments is 6 µA. In such instances, it would not make sense to adjust the curve by decreasing the model current drain input until the model transmission date accorded with the actual transmission date, as the medical device would not operate under less-than-zero-workload conditions. A common explanation for such instances is that the battery voltage value at implant was significantly higher than normal (e.g., significantly higher than a mean manufacturing value of 3.25 volts) and that the actual transmission date was relatively early. Another common explanation for such instances is that there was a recent change from a low setting to a high setting in the medical device. If the curve is based on a high setting, it will produce an earlier model replacement date.

Figure 8:
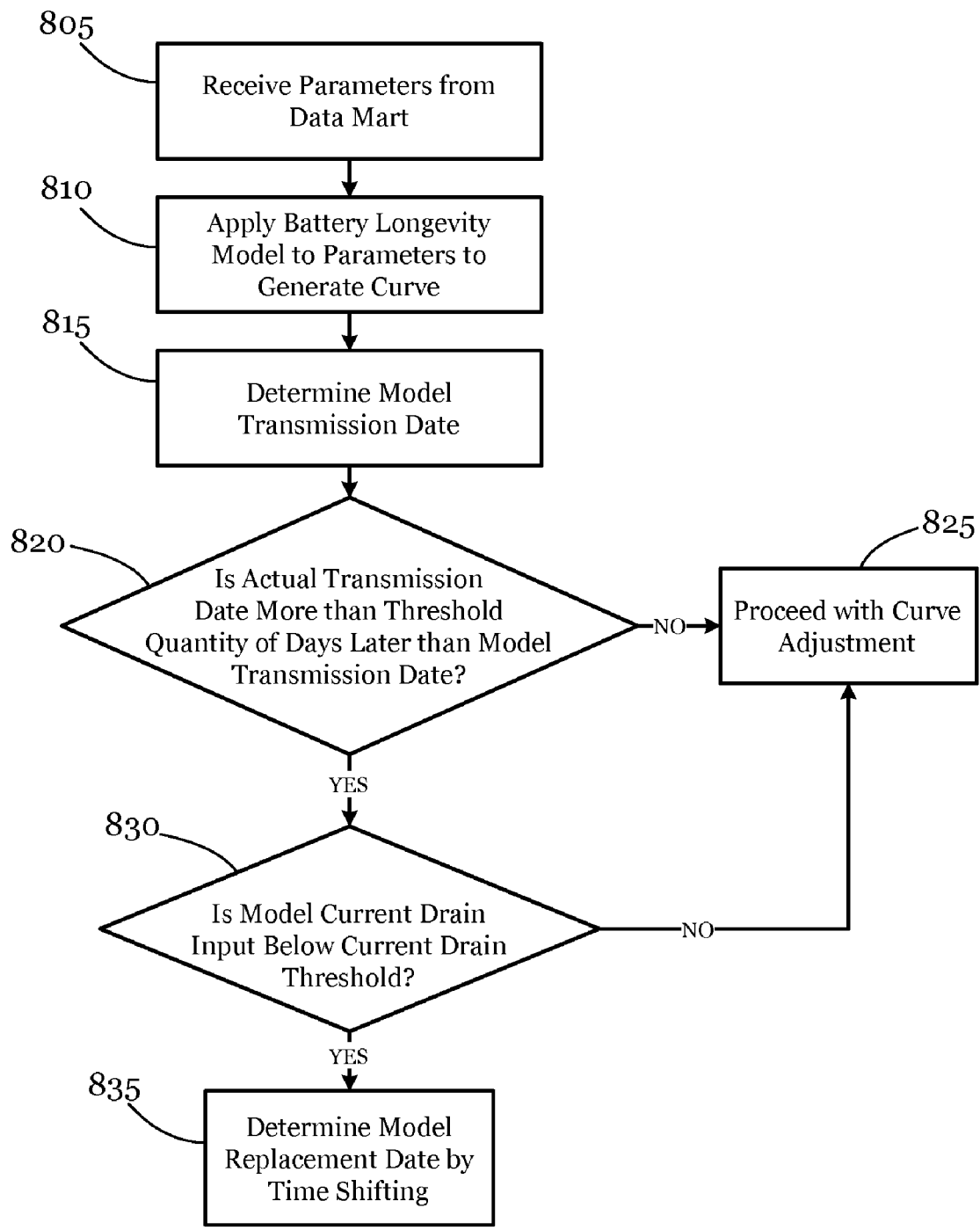
FIG. 8 is a flow chart of an illustrative method for enhancing the curve adjustment method of FIG. 2.

FIG. 8 shows an illustrative method for enhancing the curve adjustment method of FIG. 2. As with the method of FIG. 2, the method of FIG. 8 can be performed by a processor/computer according to instructions programmed in a computer-readable medium. The method of FIG. 8 includes receiving parameters from a data mart (805), applying a battery longevity model to at least some of the parameters to generate a curve (810), and determining a model transmission date (815). Such steps can have similar characteristics to corresponding steps in the method of FIG. 2.

Referring again to FIG. 8, the processor/computer performing the method can determine whether the actual transmission date is more than a threshold quantity of days later than the model transmission date (820). If the actual transmission date is not more than a threshold quantity of days later than the model transmission date, the processor/computer can proceed to the curve adjustment method of FIG. 2 (e.g., to step 220) (825). Referring again to FIG. 8, if the actual transmission date is more than a threshold quantity of days later than the model transmission date, it can be determined whether the model current drain input is below a current drain threshold (830). If the model current drain input is not below the current drain threshold, the processor/computer can proceed to the curve adjustment method of FIG. 2 (e.g., to step 220) (825).

Figure 9:
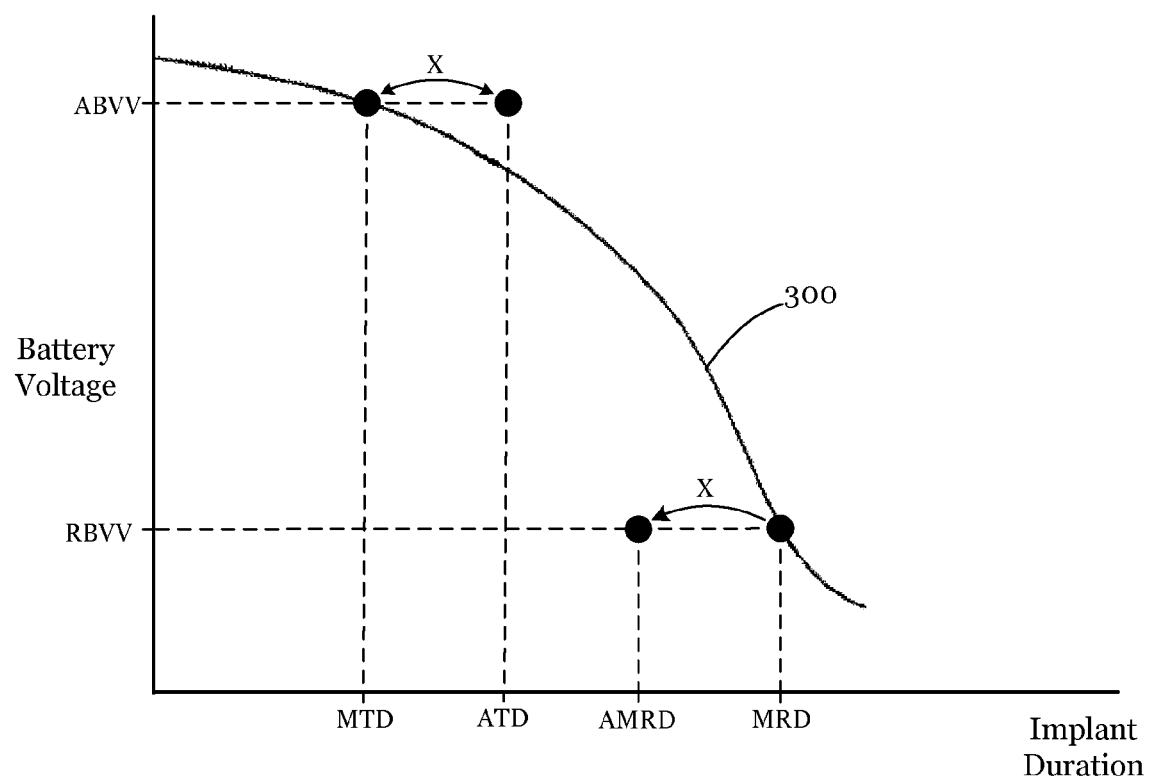
FIG. 9 is a graph showing an illustrative way to adjust a model replacement date by time shifting.

If it is determined that the actual transmission date is more than a threshold quantity of days later than the model transmission date and the model current drain input is below a current drain threshold, the model replacement date can be determined by time shifting (835). FIG. 9 provides an illustration of time shifting. As can be seen, the actual transmission date (ATD) is X days later than the model transmission date (MTD). For purposes of this illustration, assume that X days is more than the threshold quantity of days and that the model current drain input is below the current drain threshold. Instead of adjusting the curve 300 so that the model transmission date (MTD) accords with the actual transmission date (ATD), the processor/computer can determine the model replacement date (MRD) without adjusting the curve 300. Then, the model replacement date (MRD) can be adjusted, e.g., by subtracting X days from the model replacement date (MRD), thereby producing an adjusted model replacement date (AMRD). In this way, the ratio of implant duration to estimated total service time decreases only slightly, while making the adjusted model replacement date (AMRD) more accurate.

Figure 10:
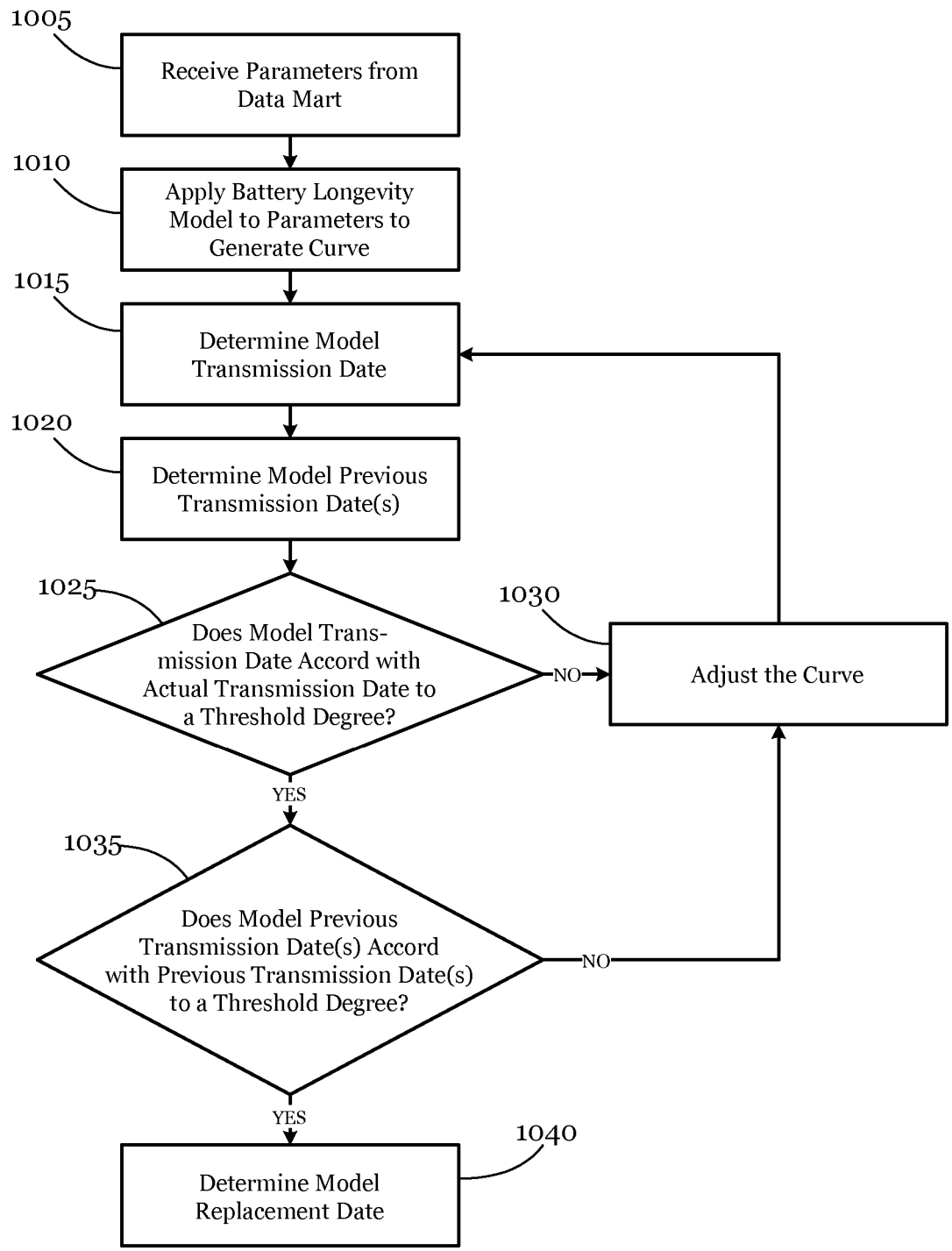
FIG. 10 is a flow chart of an illustrative method for enhancing the curve adjustment method of FIG. 2.

As is alluded to above, historical data can enhance the accuracy of the battery longevity model in some embodiments of the present invention. FIG. 10 shows an illustrative method for enhancing the curve adjustment method of FIG. 2. As with the method of FIG. 2, the method of FIG. 10 can be performed by a processor/computer according to instructions programmed in a computer-readable medium. The method of FIG. 10 includes receiving parameters from a data mart (1005), applying a battery longevity model to at least some of the parameters to generate a curve (1010), and determining a model transmission date (1015). Such steps can have similar characteristics to corresponding steps in the method of FIG. 2.

Referring again to FIG. 10, in some embodiments, the parameters received from the data mart include at least one previous battery voltage value that was provided by the medical device to the data mart on at least one previous transmission date. The model previous transmission date(s) can correspond to how many days after implantation it would take for the battery voltage to deplete to the previous battery voltage value if the battery depleted according to the curve. The processor/computer can determine a model previous transmission date by finding the previous battery voltage value on the curve.

In some embodiments, the curve can be adjusted until it accords with both the actual transmission date and the previous transmission date to a threshold degree. As shown in FIG. 10, it can be determined whether the model transmission date accords with the actual transmission date to a threshold degree (1025). If the model transmission date does not accord with the actual transmission date to a threshold degree, the curve can be adjusted (1030) in one or more iterations until the model transmission date does accord with the actual transmission date to a threshold degree. If the model transmission date does accord with the actual transmission date to a threshold degree, it can be determined whether the model previous transmission date accords with the previous transmission date to a threshold degree (1035). If the model previous transmission date does not accord with the previous transmission date to a threshold degree, the curve can be adjusted (1030) in one or more iterations until the model previous transmission date does accord with the previous transmission date to a threshold degree. If the model previous transmission date does not accord with the previous transmission date to a threshold degree, the model replacement date can be determined. In this way, the previous battery voltage value can help verify the accuracy of the curve produced by the battery longevity model and the actual battery voltage value. In some embodiments, the model replacement date determined by adjusting the curve to accord with the actual transmission date and one or more previous transmission dates can be adjusted, as is discussed in greater detail elsewhere herein.

The method of FIG. 10 is only illustrative. The curve can be adjusted in any suitable way to accord with the actual transmission date and the previous transmission date to a threshold degree. In some embodiments, the curve can be adjusted to accord with a plurality of previous transmission dates. In some embodiments, historical information, such as one or more previous transmission dates, is retrieved from the data mart only if the model replacement date based on the originally received parameters suggests that further investigation into an issue should be performed. In such cases, the historical information can be part of the further investigation.

In some embodiments described herein, the model replacement date (or adjusted model replacement date) is provided to one or more customers, while in other embodiments, the model replacement date (or adjusted model replacement date) is not provided to customers. In most cases, it is desirable to provide customers only with information that is relevant to caring for their patients. In some cases, the model replacement date (or adjusted model replacement date), and/or the condition(s) indicated by such dates, is relevant to customers in caring for their patients, while in other cases, it is not necessarily.

Figure 11:
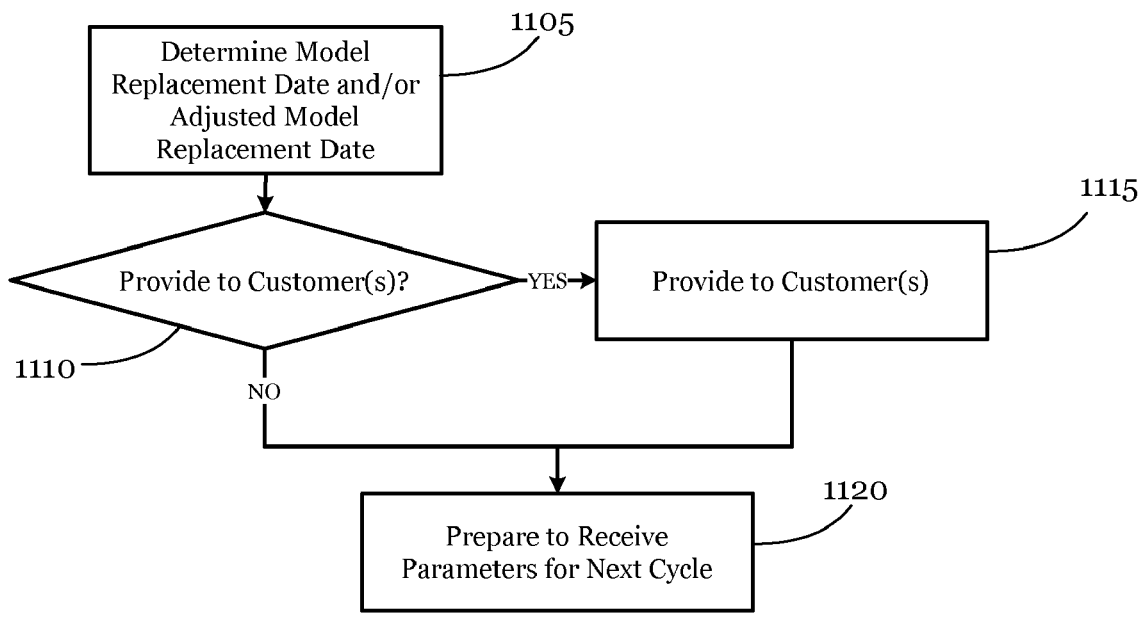
FIG. 11 is a flow chart of an illustrative method for determining whether to provide the model replacement date (or adjusted model replacement date) to one or more customers.

FIG. 11 shows an illustrative method for determining whether to provide the model replacement date (or adjusted model replacement date) to one or more customers. As with the other methods discussed herein, the method of FIG. 11 can be performed by a processor/computer according to instructions programmed in a computer-readable medium. As shown, a model replacement date and/or adjusted model replacement date can be determined (1105) according to any of the methods discussed herein. The processor/computer can then determine whether to provide that date to one or more customers (1110). For example, if the model replacement date and/or adjusted model replacement date indicate that the medical device battery is depleting prematurely, one or more appropriate customers can be alerted. If it is determined that the model replacement date and/or adjusted model replacement date should be provided to one or more customers, the processor/computer can provide the date(s) to the appropriate customer(s) (1115). Once these determinations have been made and carried out, the processor/computer can prepare to receive parameters for the next cycle of estimating when to replace a battery of a medical device that is implanted in a patient (1120).

Various implementations of the systems and methods described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) include machine instructions for a programmable processor, and can be implemented in a high-level procedural and/or object-oriented programming language, and/or in assembly/machine language. As used herein, the term "compute-readable medium" refers to any computer program product, apparatus and/or device (e.g., magnetic discs, optical disks, memory, Programmable Logic Devices (PLDs)) used to provide instructions and/or data to a programmable processor, including a computer-readable medium that receives instructions as a computer-readable signal. The term "computer-readable signal" refers to any signal used to provide instructions and/or data to a programmable processor.

In the foregoing detailed description, the invention has been described with reference to specific embodiments. However, it may be appreciated that various modifications and changes can be made without departing from the scope of the invention as set forth in the appended claims. Thus, some of the features of preferred embodiments described herein are not necessarily included in preferred embodiments of the invention which are intended for alternative uses.

What is claimed is:

1. A non-transitory computer-readable storage medium comprising instructions for causing a programmable processor to:
   receive a plurality of parameters from a data mart, the plurality of parameters including at least some parameters having been provided by a medical device implanted in a patient to the data mart on an actual transmission date, the parameters including an actual battery voltage value as of the actual transmission date;
   generate a curve indicating how a battery of the medical device implanted in the patient will deplete over time by at least applying a battery longevity model to the plurality of parameters, the curve including a model battery voltage versus a model medical device implant duration;
   determine a model transmission date by finding the actual battery voltage value on the curve;
   compare the model transmission date with the actual transmission date;
   adjust the curve until the model transmission date accords with the actual transmission date to a threshold degree; and
   determine a model replacement date by finding a replacement battery voltage value on the curve.

2. The non-transitory computer-readable storage medium of claim 1, wherein adjusting the curve comprises increasing a model current drain input if the actual transmission date is earlier than the model transmission date.

3. The non-transitory computer-readable storage medium of claim 1, wherein adjusting the curve comprises decreasing a model current drain input if the actual transmission date is later than the model transmission date.

4. The non-transitory computer-readable storage medium of claim 1, further comprising instructions for causing a programmable processor to:
   determine the model replacement date without adjusting the curve if the actual transmission date is (i) earlier than a threshold date and (ii) more than a threshold quantity of days earlier than the model transmission date; and
   adjust the model replacement date by adding to the model transmission date a quantity of days that corresponds to the difference between the model transmission date and the actual transmission date.

5. The non-transitory computer-readable storage medium of claim 1, further comprising instructions for causing a programmable processor to notify a customer if (i) the actual transmission date is earlier than a threshold date and (ii) the actual battery voltage value is below a threshold value.

6. The non-transitory computer-readable storage medium of claim 1, wherein the parameters received from the data mart include a previous battery voltage value that was provided by the medical device to the data mart on a previous transmission date, the computer-readable medium further comprising instructions for causing a programmable processor to (i) determine a model previous transmission date by finding the previous battery voltage value on the curve, (ii) compare the model previous transmission date with the previous transmission date, and (iii) adjust the curve until the model previous transmission date accords with the previous transmission date to a threshold degree.

7. The non-transitory computer-readable storage medium of claim 1, further comprising instructions for causing a programmable processor to provide the model replacement date to a customer.

8. A computer-implemented method comprising the steps of:
   receiving a plurality of parameters from a data mart, the plurality of parameters including at least some parameters having been provided by a medical device implanted in a patient to the data mart on an actual transmission date, the parameters including an actual battery voltage value as of the actual transmission date as well as other information related to the medical device and/or to the patient;
   generate a curve indicating how a battery of the medical device implanted in the patient will deplete over time by at least applying a battery longevity model to the plurality of parameters, the curve including a model battery voltage versus a model medical device implant duration;
   determining a model transmission date by finding the actual battery voltage value on the curve;
   comparing the model transmission date with the actual transmission date;
   adjusting the curve until the model transmission date accords with the actual transmission date to a threshold degree; and
   determining a model replacement date by finding a replacement battery voltage value on the curve.

9. The computer-implemented method of claim 8, wherein adjusting the curve comprises increasing a model current drain input if the actual transmission date is earlier than the model transmission date.

10. The computer-implemented method of claim 8, wherein adjusting the curve comprises decreasing a model current drain input if the actual transmission date is later than the model transmission date.

11. The computer-implemented method of claim 8, further comprising:
determining the model replacement date without adjusting the curve if the actual transmission date is (i) earlier than a threshold date and (ii) more than a threshold quantity of days earlier than the model transmission date; and
adjusting the model replacement date by adding to the model transmission date a quantity of days that corresponds to the difference between the model transmission date and the actual transmission date.

12. The computer-implemented method of claim 8, further comprising:
determining the model replacement date without adjusting the curve if (i) the actual transmission date is more than a threshold quantity of days later than the model transmission date (ii) a model current drain input is below a current drain threshold; and
adjusting the model replacement date by subtracting from the model transmission date a quantity of days that corresponds to the difference between the actual transmission date and the model transmission date.

13. The computer-implemented method of claim 8, wherein the parameters received from the data mart include a previous battery voltage value that was provided by the medical device to the data mart on a previous transmission date, the computer-implemented method further comprising (i) determining a model previous transmission date by finding the previous battery voltage value on the curve, (ii) comparing the model previous transmission date with the previous transmission date, and (iii) adjusting the curve until the model previous transmission date accords with the previous transmission date to a threshold degree.

14. The computer-implemented method of claim 8, further comprising providing the model replacement date to a customer.

15. A system comprising:
a data mart adapted to receive and store data provided by a medical device implanted in a patient;
receiving means for receiving a plurality of parameters from the data mart, the plurality of parameters including at least some parameters having been provided by the medical device implanted in the patient to the data mart on an actual transmission date, the parameters including an actual battery voltage value as of the actual transmission date as well as other information related to the medical device and/or to the patient; and
modeling means for (a) generating a curve indicating how a battery of the medical device implanted in the patient will deplete over time by at least applying a battery longevity model to the plurality of parameters, the curve including a model battery voltage versus a model medical device implant duration, (b) determining a model transmission date by finding the actual battery voltage value on the curve, (c) comparing the model transmission date with the actual transmission date, (d) adjusting the curve until the model transmission date accords with the actual transmission date to a threshold degree, and (e) determining a model replacement date by finding a replacement battery voltage value on the curve.

16. The system of claim 15, wherein the modeling means is adapted to adjust the curve by (i) increasing a model current drain input if the actual transmission date is earlier than the model transmission date or (ii) decreasing the model current drain input if the actual transmission date is later than the model transmission date.

17. The system of claim 15, wherein the modeling means is further adapted to:
determine the model replacement date without adjusting the curve if the actual transmission date is (i) earlier than a threshold date and (ii) more than a threshold quantity of days earlier than the model transmission date; and
adjust the model replacement date by adding to the model transmission date a quantity of days that corresponds to the difference between the model transmission date and the actual transmission date.

18. The system of claim 15, wherein the modeling means is further adapted to:
determine the model replacement date without adjusting the curve if (i) the actual transmission date is more than a threshold quantity of days later than the model transmission date (ii) a model current drain input is below a current drain threshold; and
adjust the model replacement date by subtracting from the model transmission date a quantity of days that corresponds to the difference between the actual transmission date and the model transmission date.

19. The system of claim 15, wherein the parameters received by the receiving means include a previous battery voltage value that was provided by the medical device to the data mart on a previous transmission date, the modeling means being further adapted to (i) determine a model previous transmission date by finding the previous battery voltage value on the curve, (ii) compare the model previous transmission date with the previous transmission date, and (iii) adjust the curve until the model previous transmission date accords with the previous transmission date to a threshold degree.

20. The system of claim 15, further comprising notifying means for providing the model replacement date to a customer.

* * * * *